(12) United States Patent
Dunn

(10) Patent No.: US 12,697,032 B2
(45) Date of Patent: Aug. 4, 2026

(54) BIOFEEDBACK SYSTEM AND METHOD FOR MONITORING ANIMAL LIMBS

(71) Applicant: IntellaTherapy, LLC, Midland, TX (US)

(72) Inventor: Allison Dunn, Cave Springs, GA (US)

(73) Assignee: IntellaTherapy, LLC, Midland, TX (US)

( * ) Notice: Subject to any disclaimer, the term of this patent is extended or adjusted under 35 U.S.C. 154(b) by 132 days.

(21) Appl. No.: 17/383,243

(22) Filed: Jul. 22, 2021

(65) Prior Publication Data

US 2023/0025180 A1 Jan. 26, 2023

(51) Int. Cl.
*A61B 5/01* (2006.01)
*A61B 5/00* (2006.01)

(52) U.S. Cl.
CPC .............. *A61B 5/01* (2013.01); *A61B 5/6828* (2013.01); *A61B 5/6831* (2013.01); *A61B 5/742* (2013.01); *A61B 2503/40* (2013.01); *A61B 2562/046* (2013.01)

(58) Field of Classification Search
CPC ....... A61B 5/01; A61B 5/6828; A61B 5/6831; A61B 5/742; A61B 2503/40; A61B 2562/046; A61B 5/0008; A01K 29/005
See application file for complete search history.

(56) References Cited

U.S. PATENT DOCUMENTS

| | | | | |
|---|---|---|---|---|
| 3,581,570 | A * | 6/1971 | Wortz | G01J 5/04 |
| | | | | 600/549 |
| 6,348,039 | B1 * | 2/2002 | Flachman | A61B 18/18 |
| | | | | 600/549 |
| 2003/0199783 | A1 * | 10/2003 | Bloom | A61B 5/445 |
| | | | | 600/549 |
| 2005/0245839 | A1 * | 11/2005 | Stivoric | A61B 10/0012 |
| | | | | 374/E1.004 |
| 2016/0058379 | A1 * | 3/2016 | Menkes | G16H 50/30 |
| | | | | 600/301 |
| 2017/0079868 | A1 * | 3/2017 | Reid, Jr. | A61B 5/6812 |
| 2019/0046033 | A1 * | 2/2019 | Gannon | G01K 1/024 |
| 2019/0374387 | A1 * | 12/2019 | Ribble | A61F 13/0209 |
| 2020/0113728 | A1 * | 4/2020 | Spector | A61B 5/02055 |
| 2022/0273115 | A1 * | 9/2022 | Karschnik | A47C 27/083 |

* cited by examiner

*Primary Examiner* — Justin Xu
*Assistant Examiner* — Jonathan M Haney

(57) ABSTRACT

A biofeedback system for monitoring a limb of an animal. The biofeedback system comprises a non-rigid wrap configured to encircle the limb when the non-rigid wrap is attached to the limb and a plurality of sensors configured to be disposed within an interior of the non-rigid wrap when the non-rigid wrap is attached to the limb. Each of the plurality of sensors measures a first biometric value. The biofeedback system further includes a control module disposed within the interior of the non-rigid wrap and coupled to the plurality of sensors. The control module reads from each of the plurality of sensors first biometric values recorded during exercise of the animal.

12 Claims, 6 Drawing Sheets

BIOFEEDBACK SYSTEM AND METHOD FOR MONITORING ANIMAL LIMBS

TECHNICAL FIELD

The present application relates generally to animal medical devices and, more specifically, to a biofeedback system for monitoring temperatures on two or more limbs of an animal to detect potential injuries.

BACKGROUND

During the training of a horse and its participation in competitions, it is important to monitor the health of the horse and its recovery from any injuries. Training stresses the relevant aspects of the equine physiology so that it can adapt to an increasingly higher level of exertion and performance. The danger therein is that the person executing the training regimen has no way of knowing with any certainty if the training is effective over time, or if the training is causing the equine to experience negative physiological reactions, such as overexertion, overheating, or creating undue stress on a particular anatomical component, thus compromising the health of the horse.

Injuries can also occur spontaneously during turn out or training. One leading cause of injury is improper practices in training that do not allow for increased oxygen and blood flow to muscles and the surrounding tissues and structures. Conventionally, a trainer determines if a horse is warmed-up based on the time the horse has been ridden and the feel of movement. Using tactile sensation by running hands over a body part if injury or discomfort is suspected has long been the standard for first sign of injury. This detection method causes small injuries to go unnoticed as small lesions attribute to a 1 or 2 degree temperature increase, which human hands are incapable of detecting. Because of the physiological oversight attributed to this method, enough time may pass such that a small manageable injury becomes a much more painful and problematic injury, requiring more recovery than would have been needed, or possible loss of use of the equine.

Medical monitoring systems provide biofeedback information to avoid compromising training and health. Information gathered about equine physiological status improves understanding of the equine's experience during exercise. Anatomical differences in blood flow, connective tissues and bodily sectors may vary greatly. Thus, recording bodily temperatures in an isolated area of a limb is paramount to proper monitoring. By way of example, temperature readings from the lower legs can differ significantly from readings above the hock joint due to vascular differences and blood flow from larger musculature. However, due to the extremely mobile nature of the equine lower limb, the stiff and immovable housings used in conventional equine monitoring systems cause temperature readings to vary considerably through each round of application due to the immobility of, and heat trapped within, the housing. This reduces its effectiveness for monitoring equine temperatures.

Therefore, there is a need in the art for an improved biofeedback system for monitoring temperatures in the limbs of an equine or other animal in order to detect potential injuries.

SUMMARY

To address the above-discussed deficiencies of the prior art, it is a primary object of the present disclosure to provide a biofeedback system for monitoring a limb of an animal. The biofeedback system comprises: i) a non-rigid wrap configured to encircle the limb when the non-rigid wrap is attached to the limb; ii) a plurality of sensors configured to be disposed within an interior of the non-rigid wrap when the non-rigid wrap is attached to the limb, wherein each of the plurality of sensors measures a first biometric value; and iii) a control module configured to be disposed within the interior of the non-rigid wrap and coupled to the plurality of sensors, wherein the control module reads from each of the plurality of sensors first biometric values recorded during exercise of the animal.

In one embodiment, each of the plurality of sensors aligns with a corresponding specific location of interest on the limb when the non-rigid wrap is attached to the limb.

In another embodiment, the plurality of sensors comprises a non-rigid wired network of sensors.

In still another embodiment, the biofeedback system further comprises a perforated foam lining that supports the plurality of sensors such that each of the plurality of sensors aligns with the corresponding specific location of interest on the limb when the non-rigid wrap is attached to the limb.

In yet another embodiment, the biofeedback system further comprises a perforated fabric layer disposed between the limb and the perforated foam lining.

In a further embodiment, the biofeedback system further comprises at least one closure associated with the non-rigid wrap that securely attaches the non-rigid wrap to the limb when the non-rigid wrap encircles the limb.

In a still further embodiment, the at least one closure comprises a hook and loop closure.

In a yet further embodiment, the biofeedback system further comprises a wearable user device configured to communicate wirelessly with the control module, wherein the wearable user device receives from the control module the first biometric values recorded during exercise of the animal.

In one embodiment, the wearable user device is configured to display processed data values associated with the first biometric values recorded during exercise of the animal.

In another embodiment, the wearable user device is further configured to receive first biometric values received from a second non-rigid wrap attached to a second limb of the animal.

It is another primary object of the present disclosure to provide a method of monitoring the limbs of an animal. The method comprises attaching a first non-rigid wrap to a first limb; ii) attaching a second non-rigid wrap to a second limb. Each of the first and second non-rigid wraps comprises a plurality of sensors, wherein each of the plurality of sensors measures a temperature at a specific location on one of the first and second limbs. The method comprises further comprises recording temperature values in the first and second non-rigid wraps during exercise of the animal and transferring the recorded temperature values from the first and second non-rigid wraps to a wearable user device, In one embodiment, the method further comprises displaying in the wearable user device processed data values associated with the recorded temperature values recorded during exercise of the animal.

In another embodiment, the method further comprises, in the wearable user device, comparing a first temperature value associated with a first specific location on the first limb with a first temperature threshold value to determine a physiological condition of the animal.

In still another embodiment, the method further comprises, in the wearable user device, comparing a second temperature value associated with a second specific location on the second limb with the first temperature threshold value to determine a physiological condition. The second specific location on the second limb corresponds to the first specific location on the first limb.

In yet another embodiment, the method further comprises, in the wearable user device, determining a difference between the first temperature value and the second temperature value and corn comparing the difference to a second temperature threshold value to determine a physiological condition of the animal.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" or "control module" means any device, system or part thereof that controls at least one operation, such a device may be implemented in hardware, firmware or software, or some combination of at least two of the same. It should be noted that the functionality associated with any particular controller or control module may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged biofeedback system.

The present disclosure describes a biofeedback system comprising a network of sensors disposed within a non-rigid wrap that transmits physiological readings to a wearable user device. The biofeedback system displays physiological data markers in real time, showing temperature readouts of the critical structures of the lower limb, inclusive of bone, tendon, and ligament. This comprehensive monitoring allows for control and intervention for health management. Once the wearable user device receives a transmission, the monitor executes an app that records and evaluates the physiological data markers. The app compares data from multiple wraps on two or more animal limbs during each use, resulting in accurate baseline data readings for each animal benefiting.

The free-forming and flexible nature of the non-rigid wrap provide free movement of the limb and ventilation to prevent the trapping of body heat. The strategically placed network of biofeedback sensors in the wrap allows for accurate temperature readings for one specific, corresponding physical anatomical structure of the equine lower leg without discounting total movement from the biomechanical movement of the whole body of the equine.

In an advantageous embodiment, there may be an additional sensor that may determine the ambient temperature at the time of a training session to help track the environmental factor contribution to physiological stress on a given anatomical structure. The disclosed wrap may take an average from an assigned group of sensors and generate an alert if a sensor detects an abnormal reading. This may be done at a high level on the wearable user device and may also analyzed in greater detail on a remote server. The wrap may begin to read data when it is attached to the animal limb and may track the gradual warm-up and cool down of the limb. The wrap records average readings and may alert to discrepancies, whether in a group of sensors on a given limb or between different limbs. Thus, the disclosed system is configured to notify the user if a first leg is hotter than a second leg or if a first area of one leg is hotter than a second area of the same leg.

Although the embodiment of the biofeedback system described below is implemented on a leg of a horse, this is by way of example only, and should not be construed to limit the scope of the present disclosure or the claims below. In alternate embodiments, the biofeedback system may be deployed on limbs of cattle, bison, deer, elk, or other mammals that are sufficiently large to wear the biofeedback system.

Figure 1:
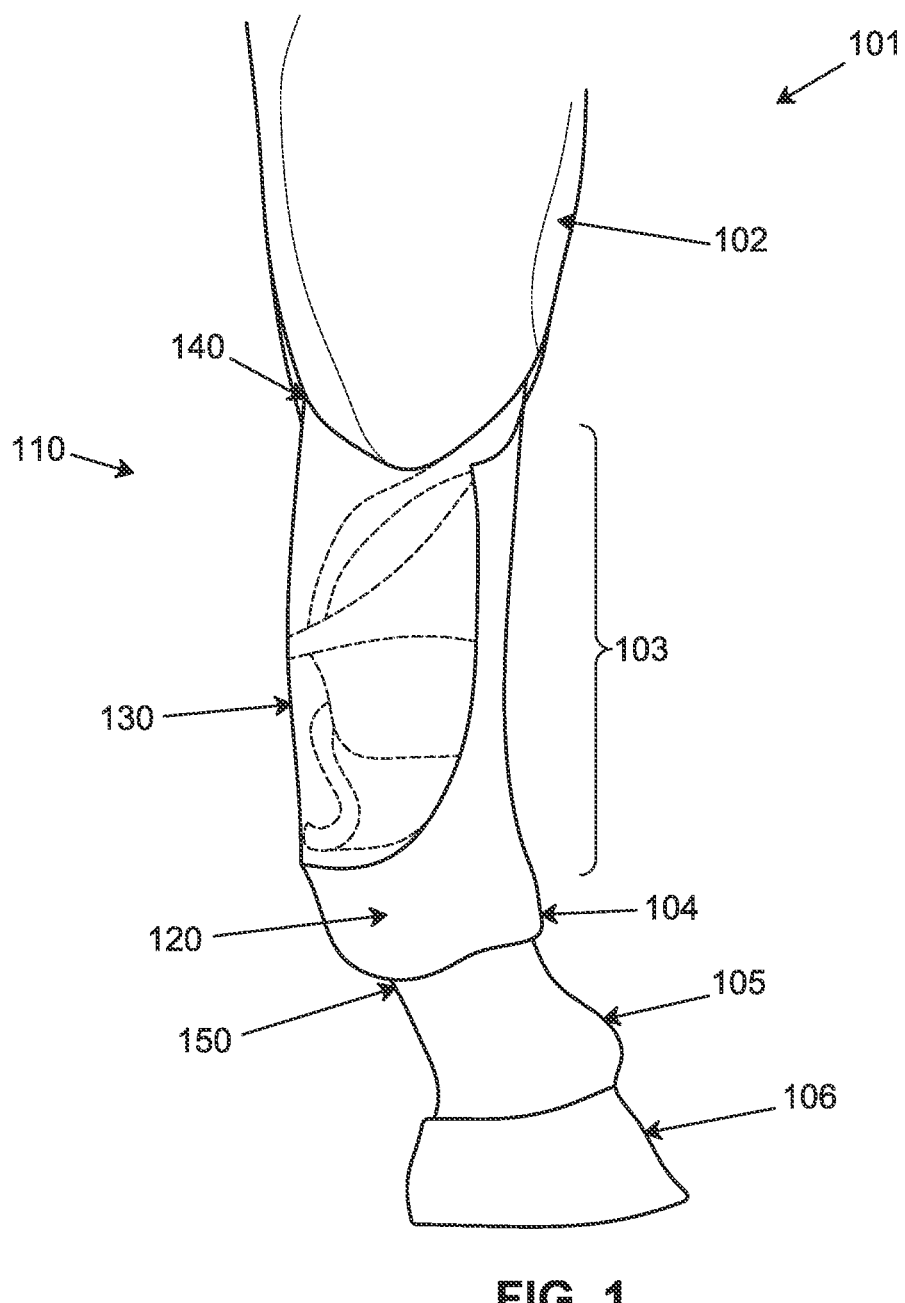
FIG. 1 illustrates a biofeedback system for monitoring an equine limb according to one embodiment of the disclosure.

FIG. 1 illustrates a biofeedback system 110 for monitoring an equine limb 101 according to one embodiment of the disclosure. The limb 101 is the lower leg of a horse. The illustrated portions of the lower leg include a knee 102, a cannon 103 (not visible), a fetlock 104, a pastern 105, and a hoof 106. Cannon 103 and fetlock 104 are covered by biofeedback system 110. The biofeedback system 110 comprises a soft, non-rigid wrap 120 that encircles the limb 101. The biofeedback system 110 further comprises a hook and loop closure 130, an upper binding 140 and a lower binding 150. Bindings 140 and 150 prevent dirt and debris from entering inside the wrap 120. In an advantageous embodiment, the hook and loop closure 130 may comprise a Velcro® closure 130 in which the loop material covers the outer surface of non-rigid wrap 120 and the hooks may disposed on a surface of linear closure straps that cling to the outer surface of non-rigid wrap 120.

Figure 2:
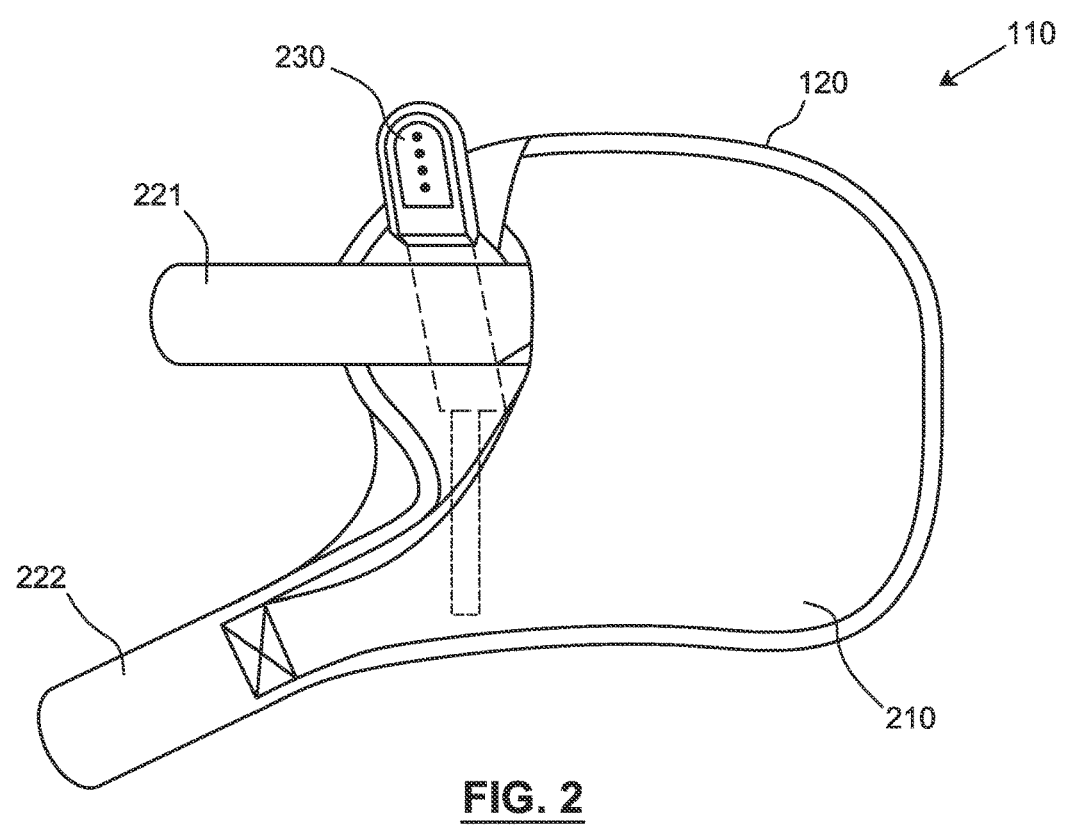
FIG. 2 illustrates a view of the exterior of the biofeedback system according to one embodiment of the disclosure.

FIG. 2 illustrates a view of the exterior of the biofeedback system 110 according to one embodiment of the disclosure. In FIG. 2, wrap 120 is unfurled to expose an outer surface 210 substantially covered by the loop material of Velcro closure 130. Wrap 120 further comprises closure straps 221 and 222. The hook material of Velcro closure 130 substantially covers closure straps 221 and 222. When an equine trainer applies wrap 120 to limb 101, closure straps 221 and 222 attach securely to outer surface 210 of wrap 120. Biofeedback system 110 further comprises a control module 230 that couples to a network of sensors (not shown) in wrap 120. As will be explained below in detail, control module 230 comprises processing circuitry, a memory, and a wireless transceiver that gathers biometric or physiological data (e.g., temperature) from limb 101 and transmits it to a wearable user device that monitors the biometric data. The biometric data may also include GPS information and ambient temperature.

Figure 3:
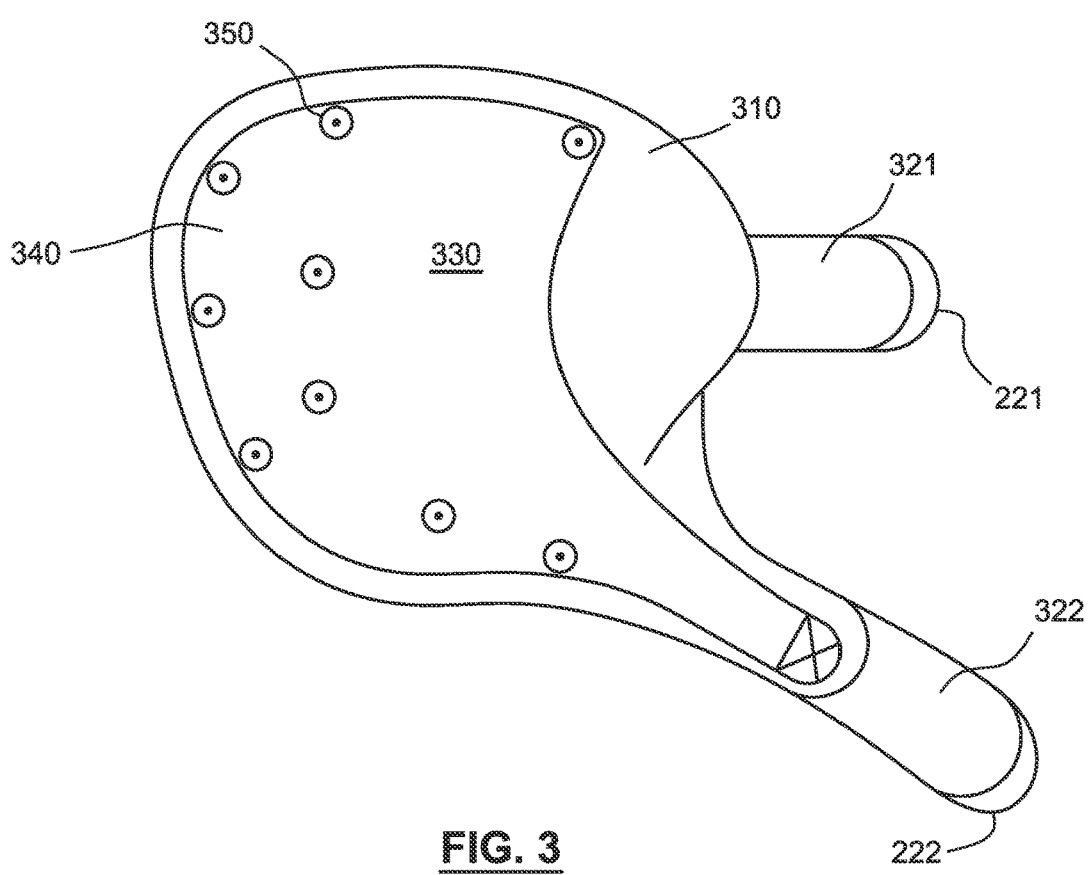
FIG. 3 illustrates a view of the interior of the biofeedback system according to one embodiment of the disclosure.

FIG. 3 illustrates a view of the interior of biofeedback system 110 according to one embodiment of the disclosure. Hook material 321 covers the inner surface of strap 221 and hook material 322 covers the inner surface of strap 222. FIG. 2 shows an inner surface 310 of wrap 120. A soft pouch assembly 330 attaches to inner surface 310 of wrap 120. Pouch assembly 330 may attach to inner surface 310 by means a Velcro closure, a plurality of buttons, snaps, or zippers, or the like. Pouch assembly 330 comprises a perforated fabric layer 340 that includes a plurality of perforations 350 that allow sensors on the inside of pouch assembly 330 to protrude through the perforations 350 to contact limb 101 of the equine.

Figure 4:
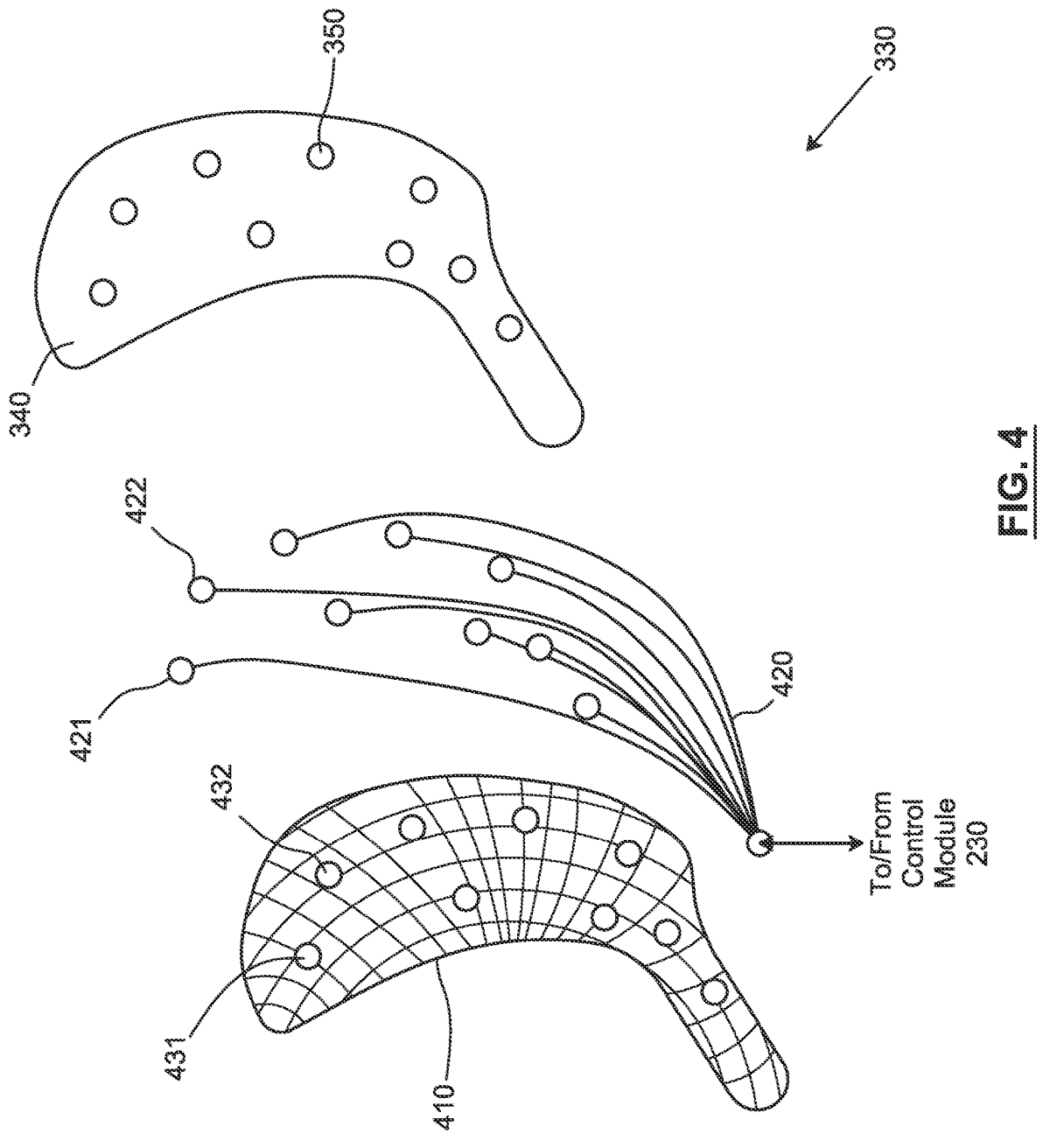
FIG. 4 illustrates an exploded view of the internal components of the biofeedback system according to one embodiment of the disclosure.

FIG. 4 illustrates an exploded view of pouch assembly 310 of biofeedback system 110 according to one embodiment of the disclosure. Biofeedback system 110 comprises a perforated foam lining 410, a wired sensor network 420, and perforated fabric layer 340. According to the principles of the present disclosure, wired sensor network 420 is disposed within and aligned with perforated foam lining 410 such that a plurality of sensors of wired sensor network 420 are aligned with, and protrude through, a plurality of perforations in perforated foam lining 410. By way of example, exemplary sensors 421 and 422 may align with exemplary perforations 431 and 432. Furthermore, perforated foam lining 410 (with wired sensor network 420 inside) is then disposed within and aligned with perforate fabric layer 340 such that the plurality of sensors of wired sensor network 420 are aligned with, and protrude through, the plurality of perforations 350 in perforated fabric layer 340. The completed pouch assembly 330 attaches to inner surface 310 of non-rigid wrap 120. The wires of wired sensor network 420 are coupled to control module 230.

When a trainer firmly attaches the non-rigid wrap 120 to limb 101, the sensors of the sensor network 420 are strategically positioned in proximity to important anatomical areas of the equine lower leg, thereby providing useful data for real world application of training and recovery methods. The positioned sensors, such as exemplary sensors 421 and 422, are flush to the lower leg, which retains free movement because of the natural and conforming shape of non-rigid wrap 120. This provides biofeedback readings that are accurate to the point of anatomy to which the sensor is applied.

The control module 230 executes a first application (or app) that provides immediate access to the biofeedback readings, which enables an accurate time estimate of a suspected injury during training. The control module 230 communicates wirelessly with a wearable user device that executes a second application that gives visual updates of current biofeedback readings in real time. The wearable user device both receives and transmits data and displays the results via a user touch screen. The wearable user device also supports a fully functional universal serial bus (USB) connector in case wireless functionality (e.g., Bluetooth) is interrupted and may further include a storage card to store data if wireless connectivity is interrupted.

Figure 5:
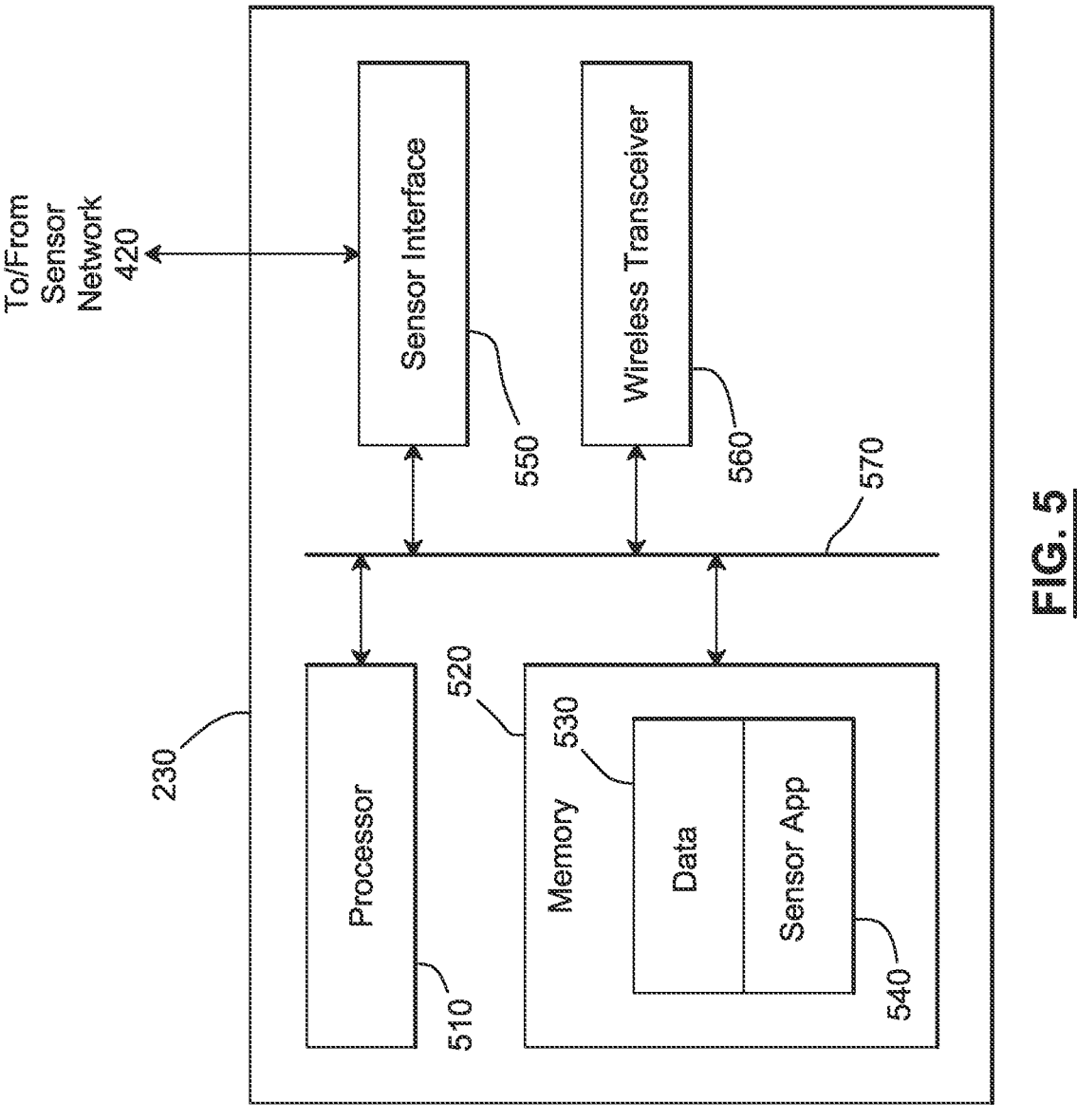
FIG. 5 illustrates a control module of the biofeedback system according to one embodiment of the disclosure.

FIG. 5 illustrates control module 230 of the biofeedback system 110 according to one embodiment of the disclosure. Control module 230 comprises processor 510, memory 520, sensor interface 550, wireless transceiver 560, and a battery and power module (not shown) that provides power to the components of control module 230. Sensor interface 550 couples to wired sensor network 420 and reads the biofeedback data (e.g., temperature) recorded by the plurality of sensors in wired sensor network 420. The components of control module 230 communicate via a common bus 570. Wireless transceiver 560 communicates wirelessly with a corresponding wireless transceiver in a wearable user device using a common wireless protocol, such as Bluetooth.

Memory 520 comprises a data storage 530 and a sensor application (or app) 540. Processor 510 executes sensor app 540 to control the overall functionality of control module 230. Under the control of sensor app 540, processor 510 reads biofeedback data from wired sensor network 420 via sensor interface 550 and stores the biofeedback data in data storage 530. Each biofeedback data value may be tagged with a time stamp and GPS stamp and stored in a directory or other data structure that corresponds to the sensor 421, 422 that reads each biofeedback data value. In this manner, the biofeedback data value can be correlated to a specific location on limb 101 proximate each sensor 421, 422. For example, temperature readings from the top of cannon 103 are tagged, labeled, and stored separately from temperature readings from the middle and the bottom of cannon 103 and from temperature readings from fetlock 104.

Figure 6:
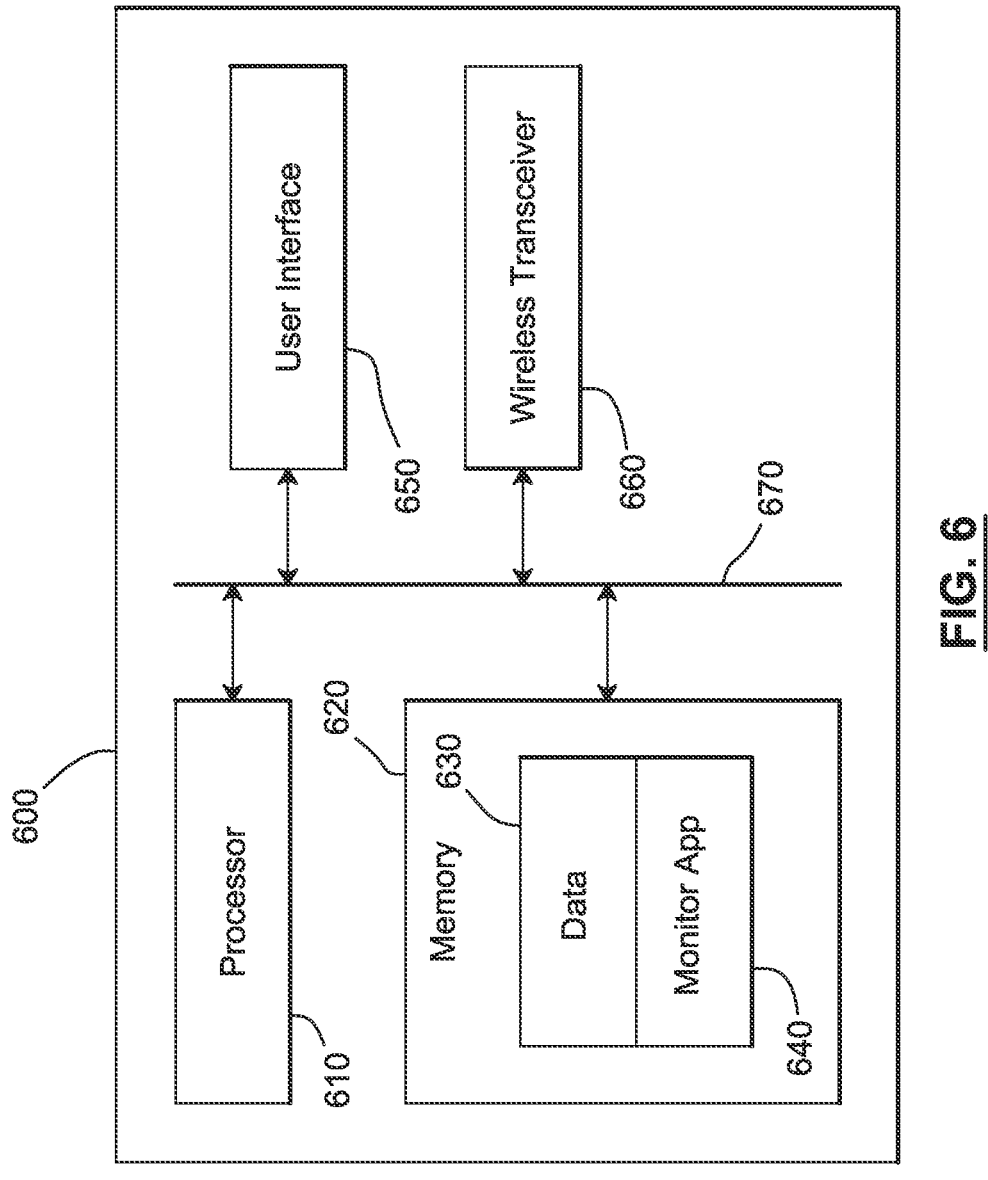
FIG. 6 illustrates a wearable user device of the biofeedback system according to one embodiment of the disclosure.

FIG. 6 illustrates a wearable user device 600 of biofeedback system 110 according to one embodiment of the disclosure. Wearable user device 600 comprises processor 610, memory 620, user interface 650, wireless transceiver 660, and a battery and power module (not shown) that provides power to the components of wearable user device 600. Wireless transceiver 660 communicates wirelessly with wireless transceiver 560 in control module 230 using a common wireless protocol, such as Bluetooth. In this manner, wearable user device 600 is configured to receive biofeedback data from data storage 530 in control module 230. User interface 650 may comprise, for example, a touch screen interface that displays data and receive touch inputs from a trainer that is operating wearable user device 600. In addition to displaying data, user interface 650 may also provide a plurality of user notifications such as audio alarms, haptic alarms, and/or visual alarms. The components of wearable user device 600 communicate via a common bus 670.

Memory 620 comprises a data storage 630 and a monitor application (or app) 640. Processor 610 executes monitor app 640 to control the overall functionality of wearable user device 600. Under the control of monitor app 640, processor 610 reads the stored biofeedback data from the data storage 530 in control module 230 via wireless transceiver 660 and stores the received biofeedback data in data storage 630. As in control module 230, each biofeedback data value in data storage 630 may be tagged with a time stamp and stored in a directory or other data structure that corresponds to the sensor 421, 422 that reads each biofeedback data value.

Thus, the biofeedback data value may still be correlated to a specific location on limb 101 proximate each sensor 421, 422.

Additionally, however, under the control of monitor app 640, processor 610 may read the stored biofeedback data from other separate control modules 230. For example, if a trainer applies a separate, non-rigid wrap 120 to each of the four limbs 101 of a horse, the wearable user device 600 may read biofeedback data from the four control modules 230 of the four wraps 120. In this manner, the data storage 630 stores biofeedback data from each of the four wraps 120 and the monitor app 640 may then compare and analyze the separate biofeedback data from the four wraps 120.

This provides a unique capability to wearable user device 600 and biofeedback system 110. If wearable user device 600 communicates with multiple control modules 230 of different wraps, wearable user device 600 not only may compare each individual biofeedback data value to a threshold value, but wearable user device 600 may also compare corresponding biofeedback data values to determine if a difference in the values exceeds a threshold value. By way of example, wearable user device 600 may compare temperature values from the fetlock 104 of each of the four limbs 101 of a horse to a first threshold value to see if any of the recorded temperature values exceeds the first threshold value. Next, wearable user device 600 may compare the difference between the temperature of the front right fetlock 104 and the temperature of the front left fetlock 104 to determine if the difference exceeds a second threshold value. In this manner, wearable user device 600 provides a trainer with additional capabilities of identifying conditions that may lead to injury to the limbs 104 of the equine.

Figure 7:
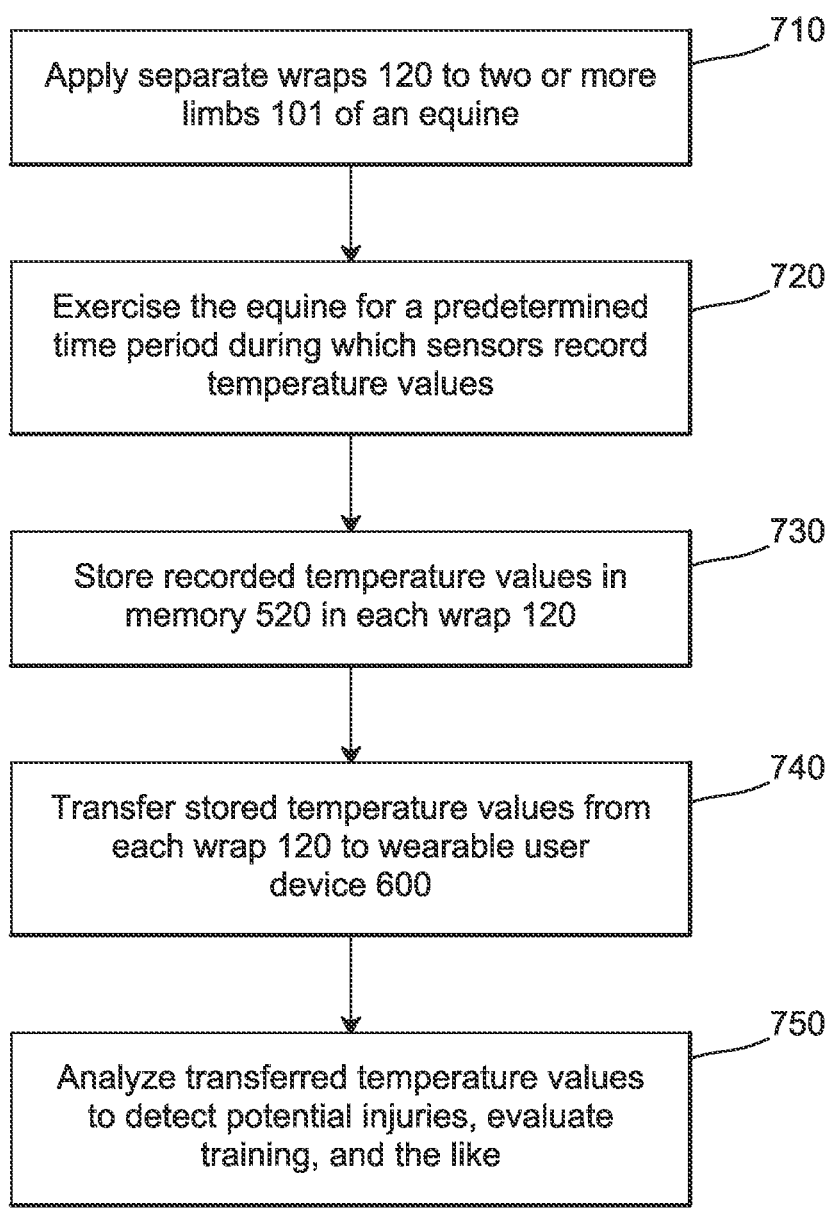
FIG. 7 is a flow diagram illustrating the operation of the biofeedback system according to one embodiment of the disclosure.

FIG. 7 is a flow diagram illustrating the operation of biofeedback system 110 according to one embodiment of the disclosure. In 710, a trainer may apply a plurality of wraps 120 to two or more limbs 101 of an equine prior to an exercise session. In 720, the trainer exercises the equine for a predetermined time period. During the exercise period, sensors in each wrap 120 record temperature values from specific locations on each limb 101. In 730, each wrap 120 stores the recorded temperature values in the memory 520 in each wrap 120. In 740, wearable user device 600 transfers the stored temperature values from each wrap 120 into the memory 620 in wearable user device 600. Finally, in 750, wearable user device 600 analyzes the transferred temperature values as described above to detect potential injuries, evaluate training, and the like. wearable user device 600 may further generate data reports that may be sent to a veterinarian, a trainer, or another party.

The disclosed wearable user device 600 and wrap 120 of the disclosed biofeedback system 110 provide access to real-time information during free-movement of the equine. The recorded biometric information, which may be temperature or another value, may be stored and reviewed in chronological order. The wearable user device 600 may compare biometric information against base-line readings for each equine without potential environmental errors introduced by a rigid housing. The information obtained from each use aids in diagnostic, recovery, and training decisions.

The placement of the sensors provides accurate feedback for all of the limb covered by the wrap 120 or for specified areas of the limb. Because of its form-fitting, non-rigid nature, wrap 120 achieves and maintains accurate placement of the sensors throughout the exercise session. Wrap 120 is not limited to a single-sensor but includes multiple anatomically placed biofeedback sensors. The sensors lay against the lower leg of the equine at strategically crucial anatomical points. The sensors may include, but are not limited to, temperature sensors, speed sensors, and impact sensors, GPS sensors.

Each sensor may report from a corresponding anatomical location to give exact information to correlate to the whole system. This leads to more precise and useful information. Because wearable user device 600 may compare temperature values, for example, against each equine baseline results, the wearable user device 600 may tailor resulting actions to each equine as an individual. The wearable user device 600 may quantify and store average values for each equine for ease of access and recollection. This is especially important because wearable user device 600 may compare stored information with newly recorded data and updated baselines as fitness, training, and/or recovery continues. Because body temperatures vary slightly within a normal range for each equine, baseline values and thresholds may be calculated based on equine individual readings.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A biofeedback system for monitoring a limb of an animal comprising:
a non-rigid perforated foam lining configured to encircle the limb when attached to the limb, the non-rigid perforated foam lining including;
a wired sensor network comprising:
a plurality of wires disposed within an interior of the non-rigid perforated foam lining; and
a plurality of sensors disposed within the interior of the non-rigid perforated foam lining, wherein the non-rigid perforated foam lining supports the plurality of sensors and the plurality of wires such that each of the plurality of sensors aligns with a perforation in the non-rigid perforated foam lining and with a corresponding specific location of interest on the limb when the non-rigid perforated foam lining is attached to the limb and each of the plurality of sensors is coupled to one of the plurality of wires;
a perforated fabric layer separate from the non-rigid perforated foam lining and configured to enclose the non-rigid perforated foam lining and the wired sensor network, wherein each of a plurality of perforations in the perforated fabric layer aligns with a perforation in the non-rigid perforated foam lining such that each of the plurality of sensors protrudes through a perforation in the perforated fabric layer to contact the specific location of interest on the limb;
a control module coupled to the plurality of sensors via the plurality of wires, wherein the control module reads from each of the plurality of sensors first biometric values recorded during exercise of the animal, and
a non-rigid wrap separate from the non-rigid perforated foam lining and the perforated fabric layer and configured to enclose the non-rigid perforated foam liming and the perforated fabric layer and encircle the limb when attached to the limb.

2. The biofeedback system as set forth in claim 1, wherein the plurality of sensors comprises a non-rigid wired network of sensors.

3. The biofeedback system as set forth in claim 1, wherein the biofeedback system further comprises at least one closure associated with the non-rigid wrap that securely attaches the non-rigid wrap to the limb when the non-rigid wrap encircles the limb.

4. The biofeedback system as set forth in claim 3, wherein the at least one closure comprises a hook and loop closure.

5. The biofeedback system as set forth in claim 1, wherein the biofeedback system further comprises a wearable user device configured to communicate wirelessly with the control module, wherein the wearable user device receives from the control module the first biometric values recorded during exercise of the animal.

6. The biofeedback system as set forth in claim 5, wherein the wearable user device is configured to display processed data values associated with the first biometric values recorded during exercise of the animal.

7. The biofeedback system as set forth in claim 6, wherein the wearable user device is further configured to receive first biometric values received from a second non-rigid wrap attached to a second limb of the animal.

8. A method for monitoring the limbs of an animal comprising:

attaching a first biofeedback system to a first limb, the first biofeedback system including:

a first non-rigid perforated foam lining configured to encircle the first limb when attached to the first limb, the first non-rigid foam lining including:

a first wired sensor network comprising:

a first plurality of wires disposed within an interior of the first non-rigid perforated foam lining; and a first plurality of sensors disposed within the interior of the first non-rigid perforated foam lining, wherein the first non-rigid perforated foam lining supports the first plurality of sensors and the first plurality of wires such that each of the first plurality of sensors aligns with a perforation in the first non-rigid perforated foam lining and with a corresponding specific location of interest on the first limb when the first non-rigid perforated foam lining is attached to the first limb and each of the first plurality of sensors is coupled to one of the first plurality of wires;

a first perforated fabric layer separate from the first non-rigid perforated foam lining and configured to enclose the first non-rigid perforated foam lining and the first wired sensor network, wherein each of a first plurality of perforations in the first perforated fabric layer aligns with a perforation in the first non-rigid perforated foam lining such that each of the first plurality of sensors protrudes through a perforation in the first perforated fabric layer to contact the specific location of interest on the first limb; and a first non-rigid wrap separate from the first non-rigid perforated foam lining and the first perforated fabric layer and configured to enclose the first non-rigid perforated foam liming and the first perforated fabric layer and encircle the first limb;

attaching a second biofeedback system to a second limb, the second biofeedback system including:

a second non-rigid perforated foam lining configured to encircle the second limb when attached to the second limb, the second non-rigid foam lining including:

a second wired sensor network comprising:

a second plurality of wires disposed within an interior of the second non-rigid perforated foam lining; and a second plurality of sensors disposed within the interior of the second non-rigid perforated foam lining, wherein the second non-rigid perforated foam lining supports the second plurality of sensors and the second plurality of wires such that each of the second plurality of sensors aligns with a perforation in the second non-rigid perforated foam lining and with a corresponding specific location of interest on the second limb when the second non-rigid perforated foam lining is attached to the second limb and each of the second plurality of sensors is coupled to one of the second plurality of wires;

a second perforated fabric layer separate from the second non-rigid perforated foam lining and configured to enclose the second non-rigid perforated foam lining and the second wired sensor network, wherein each of a second plurality of perforations in the second perforated fabric layer aligns with a perforation in the second non-rigid perforated foam lining such that each of the second plurality of sensors protrudes through a perforation in the second perforated fabric layer to contact the specific location of interest on the second limb;

a second non-rigid wrap separate from the second non-rigid perforated foam lining and the second perforated fabric layer and configured to enclose the second non-rigid perforated foam liming and the second perforated fabric layer and encircle the second limb;

recording temperature values in the first and second non-rigid wraps during exercise of the animal; and transferring the recorded temperature values from the first and second non-rigid wraps to a wearable user device.

9. The method as set forth in claim 8, further comprising:

displaying in the wearable user device processed data values associated with the recorded temperature values recorded during exercise of the animal.

10. The method as set forth in claim 8, further comprising:

in the wearable user device, comparing a first temperature value associated with a first specific location on the first limb with a first temperature threshold value to determine a physiological condition of the animal.

11. The method as set forth in claim 10, further comprising:

in the wearable user device, comparing a second temperature value associated with a second specific location on the second limb with the first temperature threshold value to determine a physiological condition of the animal, wherein the second specific location on the second limb corresponds to the first specific location on the first limb.

12. The method as set forth in claim 11, further comprising:

in the wearable user device, determining a difference between the first temperature value and the second temperature value and comparing the difference to a second temperature threshold value to determine a physiological condition of the animal.

\* \* \* \* \*